(12) United States Patent
Bigalke et al.

(10) Patent No.: US 7,964,199 B1
(45) Date of Patent: Jun. 21, 2011

(54) THERAPEUTIC COMPOSITION COMPRISING A BOTULINUM NEUROTOXIN

(75) Inventors: Hans Bigalke, Hanover (DE); Jürgen Frevert, Postdam (DE)

(73) Assignee: MERZ PHARMA GmbH & Co. KGaA, Frankfurt am Main (DE)

( * ) Notice: Subject to any disclaimer, the term of this patent is extended or adjusted under 35 U.S.C. 154(b) by 644 days.

(21) Appl. No.: 10/018,373

(22) PCT Filed: May 26, 2000

(86) PCT No.: PCT/DE00/01777
§ 371 (c)(1), (2), (4) Date: Dec. 6, 2001

(87) PCT Pub. No.: WO00/74703
PCT Pub. Date: Dec. 14, 2000

(30) Foreign Application Priority Data

Jun. 7, 1999 (DE) .................................. 199 25 739

(51) Int. Cl.
*A61K 39/08* (2006.01)
*A61K 39/00* (2006.01)
*A61K 39/02* (2006.01)
*A61K 38/00* (2006.01)

(52) U.S. Cl. ............... 424/247.1; 424/184.1; 424/234.1; 424/236.1; 530/300; 530/324

(58) Field of Classification Search ............... 424/239.1, 424/247.1, 236.1; 514/2, 21; 530/350, 363, 530/364, 825, 300, 820
See application file for complete search history.

(56) References Cited

U.S. PATENT DOCUMENTS

| | | | | |
|---|---|---|---|---|
| 5,512,547 A * | 4/1996 | Johnson et al. | ................. | 514/21 |
| 5,846,929 A | 12/1998 | Johnson et al. | | |
| 6,358,917 B1 * | 3/2002 | Carruthers et al. | ................ | 514/2 |
| 6,787,517 B1 * | 9/2004 | Gil et al. | ........................... | 514/1 |

FOREIGN PATENT DOCUMENTS

| | | |
|---|---|---|
| KR | 466407 | 1/2002 |
| WO | WO 94/26308 | 11/1994 |
| WO | WO 94/28923 | 12/1994 |
| WO | WO 95/17904 | 7/1995 |
| WO | WO 95/30431 | 11/1995 |
| WO | WO 97/35604 | 10/1997 |
| WO | WO 0074703 | 12/2000 |

OTHER PUBLICATIONS

Goeschel et al, Experimental Neurology, 147, 1997, pp. 96-102.*
Keen et al, Plastic and Reconstructive Surgery, Jul. 1994, 94, No. 1, pp. 94-99.*
Shelley et al (J Am Acad Dermatol. 1998, 28:227-9).*
Benedetto, International Journal of Dermatology, 1999, 28, 641-655.*
Goeschel et al, (Experimental Neurology, 147, 1997, pp. 96-102).*
Borodic et al (Ophthalmic Plastic and Reconstructive Surgery, vol. 9, No. 3, p. 182-190).*
Keen et al (Plastic and Reconstructive Surgery, Jul. 1994, 94, No. 1, pp. 94-99).*
Jankovic et al (The New England Journal of Medicine, Apr. 25, 1991).*
Carruthers et al, Cosmetic Uses of Botulinum Toxin A Exotoxin. In:Klein AW, ed. Tissue Augmentation in Clinical Practice: Procedures and Techniques. New York: Marcel Dekker, 1998:207-236).*
Heckman et al (Arch Dermatol, vol. 134, Oct. 1998).*
Kessler (J Neurol (1999) 246:265-274).*
Goschel et al, (Experimental Neurology, 147, 1997, pp. 96-102).*
Green et al (Movement Disorders, vol. 8, No. 4, 1993, p. 479-483).*
Carruthers et al (Basic and Clinical Dermatology, Marcel Dekker, Inc, New York, 1998, Chapter 11, pp. 207-236).*
Shelley et al (Journal of the American Academy of Dermatology, Feb. 1998, pp. 227-229).*
Webster's II New Riverside University Dictionary, The Riverside Publishing Company, 1984.*
Borodic et al (Ophthalmic Plastic and Reconstructive Surgery, 1993, vol. 9, No. 3, p. 182-190).*
Hatheway CL and Dang C, Immunogenicity of the immunotoxins of *Clostridium botulinum*. In: Jankovic J and Hallett M, eds. *Therapy with botulinum toxin*. New York: Marcel Dekker, 1994, pp. 93-97.
Greene P, Fahn S and Diamond B. 1994. Development of Resistance to *Botulinum* Toxin Type A in Patients with Torticollis. Movement Disorders 9:213-217.
Jankovic J and Schwartz K. 1995. Response and immunoresistance to *botulinum* toxin injections. Neurobiology 45:1743-1746.
Borodic, Johnson E Goodnough M and Schantz E. 1996. *Botulinum* toxin therapy, immunologic resistance, and problems with available materials. Neurology 46:26-29.
Dertzbaugh MT and West MW. 1996. Mapping of protective and cross-reactive domains of the type a neurotoxin of *Clostridium botulinum*. Vaccine 14:1538-1544.
Doellgast GJ, Brown JE, Koufman JA and Hatheway C. 1997. Sensitive Assay for Measurement of Antibodies to *Clostridium botulinum* Neurotoxins A, B, and E: Use of Hapten-Labeled Antibody Elution To Isolate Specific Complexes. J. Clinical Microbiol. 35:578-583.
Dressler D. 1997. *Botulinum* toxin therapy failure: causes, evaluation procedures and management strategies. European J. Neurology 4 (suppl 2):S67-S70.

(Continued)

*Primary Examiner* — Vanessa L. Ford
(74) *Attorney, Agent, or Firm* — Hueschen and Sage

(57) ABSTRACT

A pharmaceutical preparation comprising one of the botulinum neurotoxins from *Clostridium botulinum* of types A, B, C, D, E, F or G or a mixture of two or more of these neurotoxins, wherein the neurotoxin or the mixture of neurotoxins is free of the complexing proteins which naturally form the botulinum neurotoxin complexes together with the neurotoxins.

8 Claims, No Drawings

OTHER PUBLICATIONS

Brin MF. 1997. *Botulinum* Toxin: Chemistry, Pharmacolocy, Toxicity, and Immunology. Muscle & Nerve Supplement 6:S146-S168.

Kessler KR, Skutta M and Benecke R. 1999. Long-term treatment of cervical dystonia with *botulinum* toxin A: efficacy, safety, and antibody frequency. J. Neurol. 246:265-274.

Aoki, KR. 1999. Preclinical update on BOTOX® (*botulinum* toxin type A)-purified neurotoxin complex relative to other *botulinum* neurotoxin preparations. European Journal of Neurology 6 (suppl. 4):S3-S10.

Brashear A. 2001. The *Botulinum* Toxins in the Treatment of Cervical Dystonia. Seminars in Neurology 21:85-90.

Aoki KR and Guyer B. 2001 *Botulinum* toxin type A and other *botulinum* toxin serotypes: a comparative review of biochemical and pharmacological actions. European Journal of Neurology 8 (suppl. 5):21-29.

Jankovic J. *Botulinum* Toxin: Clinical Implications of Antigenicity and Immunoresistance. In: Brin MF, Jankovic J and Hallett M eds. *Scientific and Therapeutic Aspects of Botulinum Toxin*. Philadelphia: Lippincott Williams & Wilkins, 2002, pp. 409-415.

Aoki KR. Immunologic and Other Properties of Therapeutic *Botulinum* Toxin Serotypes. . In: Brin MF, Jankovic J and Hallett M eds. *Scientific and Therapeutic Aspects of Botulinum Toxin*. Philadelphia: Lippincott Williams & Wilkins, 2002, pp. 103-113.

Aoki KR. Physiology and Pharmacology of Therapeutic *Botulinum* Neurotoxins. In: Kreyden OP, Böni R and Burg G eds. *Hyperhidrosis and Botulinum Toxin in Dermatology*. Curr Probl Dermatol, Basel: Karger, 2002, vol. 30, pp. 107-116.

Aoki KR 2002. *Botulinum* neurotoxin serotypes A and B preparations have different safety margins in preclinical models of muscle weakening efficacy and systemic safety. Toxicon 40:923-928.

Eleopra R, Tungnoli V Quatrale R Rossetto O, Montecucco C and De Grandis D. *Botulinum* Neurotoxin Serotypes C and E: Clinical Trials. In: Brin MF, Jankovic J and Hallett M eds. *Scientific and Therapeutic Aspects of Botulinum Toxin*. Philadelphia: Lippincott Williams & Wilkins 2002, pp. 441-450.

Münchau A, Palmer JK, Dressler K, O'Sullivan JD Tsang KL, Jahanshahi M, Quinn NP, Lees AJ, Bhatia KP. 2001. Prospective study of selective peripheral denervation for *botulinum*-toxin resistant patients with cervical dystonia. Brain 124:769-83.

Wohlfahrt, et al. Proceedings of Biomedical Aspects of Clostridial neurotoxins. Intl Conference Oxford-Jul. 7-11, 1996, p. 165.

Balash, et al. European Journal of Neurology, 2004, 11:361-370.

Comella, et al. Muscle and Nerve, May 2004, vol. 29, pp. 628-644.

BOTOX® Cosmetic, Product Insert, Jan. 2005.

Dressler, D. , 2005, Latest results on non-response to conventional *botulinum* toxin treatment. Interview with PD Dr. D. Dressler, University of Rostock.

Lew, et al. Neurology, 1997, 49:701-707.

Troung, et al. Movement Disorders, 1997, 12:772-775.

Truong, et al. Movement Disorders, 1995, 10:394.

Australian Opposition 774590_BENEKE Declaration_2006.

Australian Opposition_Benecke Declaration_ANNEX_2006.

Australian Opposition 774590_FRAZER Declaration_2005.

Australian Opposition 774590_FRAZER Declaration_ANNEX_2005.

Australian Opposition 774590_NATTRASS Declaration_2006.

Australian Opposition 774590_NATTRASS Declaration_ANNEX_2006.

Australian Opposition 774590_O'Sullivan Declaration_2005.

Australian Opposition 774590_PATON Declaration_2006.

Australian Opposition 774590_PATON Declaration_ANNEX_2006.

Australian Opposition 774590_Tanks Declaration_2005.

Australian Opposition 774590_Statement of Grounds and Particulars_Jun. 12, 2007.

Dressler, et al. Archives of Pharmacology, 365: R18, 2002.

European Patent 1185291_Grounds of Opposition_2004.

European Patent 1185291_Result of Oral Proceeding_Feb. 16, 2006.

European Patent 1185291_Notice of Appeal_May 24, 2006.

European Patent 1185291_Opponent Submission_Dec. 16, 2005.

European Patent 1185291_Opponent Submission_Jan. 24, 2006.

European Patent 1185291_Patentee Submission_Aug. 3, 2007.

European Patent 1185291_Opposition Decision_Apr. 6, 2006.

European Patent 1185291_Withdrawal of Opposition_Sep. 6, 2007.

European Patent 1185291_Maintenance of Patent_Jun. 10, 2010.

Jankovic, et al. Movement Disorders, 20, P105, 2005.

Wohlfahrt, et al. In: Trunter HS, ed. Proceedings of Biomedical Aspects of Clostridial Neurotoxin Intl. Conf. Oxford, Center for Applied Microbiology and Research:165, 1996.

Chen, et al. Neurology 51:1494-1496, 1998.

Hanna, et al. J. Neurol. Neurosurg. Psychiatry 66:612-613,1999.

Sankhla, et al. Movement Disorders, 13:150-154, 1998.

Spanoyannis, et al. Development Medicine and Child Neurology 40:33 Scientific Poster:SP:8, 1998.

Opposition to Korean Patent 0466407 Opponent's Brief, Aug. 14, 2007.

Opposition to Korean Patent 0466407 Exhibit A-7, Jun. 24, 2005.

Opposition to Korean Patent 0466407 Exhibit A-12, Mar. 5, 2007.

Opposition to Korean Patent 0466407 Opponent's Brief, Feb.13, 2007.

Opposition to Korean Patent 0466407, Opponent's Brief, Jan. 30, 2007.

Opposition to Korean Patent 0466407, Opponent's Brief, May 18, 2007.

Opposition to Korean Patent 0466407, Opposition Brief, Mar. 10, 2006.

Opposition to Korean Patent 0466407, Opposition Withdrawal, Sep. 6, 2007.

* cited by examiner

THERAPEUTIC COMPOSITION COMPRISING A BOTULINUM NEUROTOXIN

The present invention relates to pharmaceutical preparations which comprise a botulinum neurotoxin from *Clostridium botulinum*, the neurotoxin being free of the complexing proteins naturally present in the complex. The direct consequence thereof is the realization, on which the present invention is based, that with the free neurotoxin, in contrast to the complex, there is only a distinctly reduced, or no, induction of neutralizing antibodies in the patient. The present invention further relates to the use of botulinum neurotoxins from *Clostridium botulinum* for producing a medicine for treating disorders of the nervous system. Another aspect of the present invention relates to the use of the botulinum neurotoxins from *Clostridium botulinum* for cosmetic treatment.

*Clostridium botulinum* toxin complex type A ($M_r$ 900,000) has been employed for several years for the therapy of various dystonias. At present two different pro-ducts comprising this complex are approved for the treatment of blepharospasm, hemifacial spasms and spasmodic torticollis: BOTOX® and DYSPORT®. Clinical trials of the therapy of other disorders of the nervous system (e.g. spasticities, migraine, low back pain, cervical spine disorders, hypersalivation) are currently in progress. The products are also employed for cosmetic indications such as hyperhidrosis and pronounced wrinkling. The other *Clostridium botulinum* toxin complexes (of types B, C, D, E, F, G) are also suitable for these therapies. However, at present there is no approved product comprising one of the type B-G toxins on the market.

Botulinum toxin complexes are composed of a mixture of clostridial proteins. These are hemagglutinins with different molecular masses, a nontoxic, non-hemagglutinating protein ($M_r$ about 120,000) and a neurotoxin ($M_r$ about 150,000). They form an acid-stable complex which is responsible for the oral toxicity in cases of food poisoning. In contrast to the pure neurotoxin, the complex resists the aggressive environment in the gastrointestinal tract and makes enteral absorption of the neurotoxin possible, and this reaches the target cells via the bloodstream or the lymphatic system and there induces blockade of transmitter release. This is followed by a paralysis of striped and smooth muscles and cessation of various autonomic functions. Poisoned patients die of respiratory muscle failure. Since the pure neurotoxin is degraded in the gastrointestinal tract and thus does not undergo enteral absorption, it is not toxic after ingestion. On parenteral administration, the therapeutic effects of the neurotoxin and of the complex do not differ since the complex decomposes into its constituents in tissue, and only the neurotoxin is taken up by the target cells.

For therapeutic use, the complex is in the current state of the art injected directly into dystonic or spastic muscles, where the neurotoxin is released at physiological pH from the complex and elicits the desired pharmacological effect. Although the complex is administered only in extremely low doses (1-25 ng, depending on indication and size of the affected muscle), repeated injection is followed in a considerable number of patients by formation of specific neutralizing antibodies which are also directed against the neurotoxin. The direct consequence is that antibody-positive patients no longer respond to the complex. However, they might be treated with other toxin types, although none of them is approved for therapy. When the patient has been tested with all the toxin types and has formed antibodies against them, further administration of a botulinum toxin complex (irrespective of the type) no longer provides a remedy. It must be taken into account in this connection that each dose of complex contributes to increasing the antibody titer until further administration of the complex no longer makes sense because no effect is now achieved. It often takes years for the antibody titer to fall significantly, so that these patients are not (cannot be) treated (with botulinum neurotoxin) for long periods.

The formation of specific antibodies is favored by two factors. On the one hand, the neurotoxin, fixed in the complex, remains in the tissue for a long period and may activate immune cells which migrate into the tissue to form antibodies. The long residence time does not result in increased uptake by the target cells, however, since poisoned target cells are no longer able to take up toxin. The neurotoxin which slowly dissociates out of the complex thus now has only immunological activity. On the other hand, the proteins present in the complex intensify an immune response. Hemagglutinins are lectins, that is to say proteins which are distinguished by a high affinity for certain sugars. Because of their binding to sugar structures, lectins have immuno-stimulating effects. Thus, it has been possible to show that the lectins concanavalin A, phytohemagglutinin and pokeweed mitogen activate T and B lymphocytes. The hemagglutinins of the botulinum toxin complexes, which likewise bind to membrane-associated sugars, are thus able in a similar way to act as immunoadjuvants and contribute to antibody formation and thus to failure of the therapy.

The object of the inventors of the present invention was therefore to develop an alternative mode of treatment of the above-mentioned disorders and disturbances. In particular, the inventors wish to propose a suitable active ingredient with which patients who have already formed neutralizing antibodies can be treated.

To achieve the object stated above, as alternative to the two commercial type A botulinum toxin complex products, BOTOX® and DYSPORT®, and also as alternative to the complexes described in the prior art of the other types (B, C, D, E, F, G), a novel pharmaceutical has been developed which comprises only pure neurotoxin (type A or B, C, D, E, F, G) and is free of hemagglutinins and other exogenous proteins. Because of its lower molecular mass, it diffuses more quickly to the target cells in which it is taken up, before immune cells, attracted by hemagglutinins, are activated. We found in antigenicity studies that the pure neurotoxin of all types—in distinction from commercial products of type A and the complexes of types B to G—induces no, or at the most very little, formation of antibodies. On therapeutic use of this newly developed pharmaceutical (pure neurotoxin of types A, B, C, D, E, F, G) there is no failure of therapy due to antibodies even after repeated administration. It has also been possible to show that the pure neurotoxins are, because of their immediate bioavailability, still suitable for the therapy of patients who have developed, after administration of a botulinum toxin complex, e.g. after treatment with BOTOX® or DYSPORT®, an antibody titer against the appropriate type (so-called secondary non-responders), that is to say are no longer amenable to further treatment with BOTOX® or DYSPORT®, because administration of the commercial toxins no longer alleviates the symptoms.

The pharmaceutical provided according to the invention is suitable as therapeutic composition in particular for patients who exhibit an antibody titer against a botulinum toxin, in particular against that of type A. The novel pharmaceutical (pure neurotoxin or mixture of a plurality of pure neurotoxins) is particularly suitable for patients who exhibit an antibody titer not exceeding 50, preferably not exceeding 30, more preferably not exceeding 20, particularly preferably not exceeding 10, and very particularly preferably not exceeding 5, mU/ml. In this connection, 1 mU of antibody is the amount of antibody which neutralizes 10 U of toxin.

On the other hand, the novel pharmaceutical can be employed with particular advantage for patients who have never, or not for many years, been treated with botulinum neurotoxin, because their antibody titer is low or zero from the outset. The advantage of the present invention is then that the increase in the titer in these patients due to the treatment with the pure toxin according to the present invention is zero, or at the most very insignificant. In other words, the novel therapeutic composition can be administered over long periods without losing its effect.

The induction of antibodies during therapy with a *C. botulinum* toxin is thus prevented by administering a pure neurotoxin in place of the high molecular weight toxic complexes. The neurotoxin which has been completely separated from the complex proteins is immediately bioavailable and can bind directly to the nerve endings of the motor endplates.

One aspect of the present invention thus relates to a pharmaceutical preparation which comprises at least one of the botulinum neurotoxins from *Clostridium botulinum* of types A, B, C, D, E, F or G (or a mixture of two or more of these neurotoxins), all the neurotoxins being free of the complexing proteins naturally present in the complex.

In a preferred embodiment, the pharmaceutical preparation is such that the induction of neutralizing antibodies in the patient by the neurotoxin or the mixture of neurotoxins is reduced by comparison with the complexes or is zero.

A further preferred embodiment provides a pharmaceutical preparation which comprises as neurotoxin or as mixture of neurotoxins a natural neurotoxin or a mixture of natural neurotoxins.

A further preferred embodiment provides a pharmaceutical preparation which comprises as neurotoxin or as mixture of neurotoxins a recombinant neurotoxin or a mixture of recombinant neurotoxins.

Another preferred embodiment of the novel pharmaceutical preparation provides a preparation which comprises as neurotoxin the neurotoxin from *Clostridium botulinum* type A or B or as mixture of neurotoxins a mixture of the neurotoxins from *Clostridium botulinum* type A and B.

A further aspect of the present invention relates to the use of the botulinum neurotoxins from *Clostridium botulinum* of types A, B, C, D, E, F or G or of a mixture of two or more of these neurotoxins for producing a medicine for treating disorders of the nervous system and dystonias. The disorders of the nervous system and the dystonias are in a preferred embodiment spasmodic torticollis and blepharospasm, spasticities such as footdrop, hemifacial spasms, migraine, low back pain, cervical spine disorders or hypersalivation.

Another aspect of the present invention in turn relates to the use of the botulinum neurotoxins from *Clostridium botulinum* of types A, B, C, D, E, F or G or of a mixture of two or more of these neurotoxins for cosmetic treatment, particular preference being given to a cosmetic treatment for treating hyperhidrosis and wrinkling, especially in the facial region.

Very particularly preferred for the purpose of the present invention is the use of one of the neurotoxins alone or in a mixture for producing a medicine for treating the above-mentioned nervous disorders in persons (preferably humans, but also animals) who already exhibit neutralizing antibodies against a botulinum neurotoxin complex, in particular against the complex of *Clostridium botulinum* type A or B, or against a plurality of complexes, in particular against the complexes of *Clostridium botulinum* type A and B (so-called secondary non-responders).

The neurotoxins, mixtures thereof and the novel pharmaceutical preparations can be in the form of an aqueous solution, in particular as aqueous solution for injection, but also as lyophilized products.

The pure neurotoxins of types A-G, which are known per se, were produced by the protocols present in the publications detailed in the list of references. The purification of two neurotoxins (type A and B) is described by way of example in the following examples.

EXAMPLE 1

Isolation of the Pure Neurotoxin

The pure neurotoxin from *Clostridium botulinum* type A is obtained by a process based on the process of DasGupta & Sathyamoorthy. *Clostridium botulinum* type A is cultivated in a 20 l fermenter in a medium consisting of 2% proteose peptone, 1% yeast extract, 1% glucose and 0.05% sodium thioglycolate. After growth for 72 hours, the toxin is precipitated by adding 3 N $H_2SO_4$ (final pH=3.5). The precipitated and centrifuged biomass is extracted with 0.2 M sodium phosphate buffer pH 6.0.

After removal of the nucleic acids by precipitation with protamine sulfate, the toxin is precipitated by adding ammonium sulfate. The precipitate which has been solubilized and dialyzed against 50 mM sodium phosphate pH 6.0 is bound to a DEAE-Sephadex column at the same pH and detached with 150 mM NaCl. This is followed by a chromatography on a QAE-Sephadex column which has been equilibrated with a 50 mM tris/HCl buffer pH 7.9. The toxin is eluted via an NaCl gradient. In the last step, the toxin is chromatographed on SP-Sephadex at pH 7.0. In this case, the bound toxin is detached from the column using an NaCl gradient (0-300 mM). The purified toxin is analyzed in an SDS polyacrylamide gel electrophoresis (SDS-PAGE) and exhibits a purity of 95±5%. The biological activity is determined in the mouse $LD_{50}$ assay: one $LD_{50}$ unit corresponds to 4.8 pb of protein.

EXAMPLE 2

Production of a Finished Pharmaceutical Containing Botulinum Neurotoxin

The purified neurotoxin from Example 1 is used to prepare a solution which comprises 200 mouse $LD_{50}$ units, 10 mg of sucrose and 2 mg of human serum albumin per ml. The solution (0.5 ml) is dispensed into vials and freeze-dried. The lyophilizates are reconstituted with physiological saline, and the biological activity is determined. The vials comprise 100±30 $LD_{50}$ units.

EXAMPLE 3

Isolation of Pure Neurotoxin B

*Clostridium botulinum* type B is cultivated in the same medium and under the same conditions as type A and is processed as far as the ammonium sulfate precipitation. This is again followed by a DEAE-Sephadex chromatography at pH 6.0. The fractions eluted from the column with 150 mM NaCl are combined and dialyzed against sodium phosphate pH 7.0, followed by a chromatography on QAE-Sephadex. The toxin-containing fractions are chromatographed further on a DEAE-Sephadex column at pH 8.5 (50 mM tris/HCl pH 8.5).

Finally, the high-purity botulinum toxin type B is obtained by a chromatography on hydroxyapatite equilibrated with 10 mM Na phosphate pH 8.0. The bound homogeneous toxin is eluted with 80 mM Na phosphate pH 8.0 and subsequently the biological activity is determined in the $LD_{50}$ assay ($2$–$4 \times 10^7$ $LD_{50}$ units/mg of protein).

EXAMPLE 4

Detection of Antibodies 20 rabbits received intracutaneous injections of 25 U of BOTOX® at intervals of 14 days over a period of 12 weeks (5 injections). Serum was obtained after 3 weeks and then at intervals of 14 days.

Antibodies against *Clostridium botulinum* neurotoxin A were detected in an enzyme immunoassay by immobilizing the homogeneous neurotoxin on a microtiter plate. Antibodies binding to the neurotoxin were quantified using a second, enzyme-labeled antibody.

The result is shown in Table 1. Antibodies were detected in 5 rabbits as little as 5 weeks after the first administration. After 11 weeks, sera from 17 rabbits, that is to say 85% of the animals employed, contained antibodies against the neurotoxin. It was shown in the biological activity assay that 12 of the 17 sera contained neutralizing antibodies (Table 2).

TABLE 1

Determination of serum samples (diluted 1:100) from rabbits treated with BOTOX ® using an enzyme immunoassay. $OD_{490}$ nm > 0.1 are indicated. All OD values are corrected for the OD values of the preimmune sera (OD about 0.150).

| Rabbit No. | 3rd week | 5th week | 7th week | 9th week | 11th week |
|---|---|---|---|---|---|
| 1 | — | — | — | 0.11 | 0.36 |
| 2 | — | — | — | 2.36 | 2.23 |
| 3 | — | — | 0.57 | 1.43 | 1.44 |
| 4 | — | — | 0.68 | 1.68 | 0.93 |
| 5 | — | 0.97 | 3.52 | 3.49 | 3.44 |
| 6 | — | — | 1.34 | 2.32 | 2.70 |
| 7 | — | — | 2.13 | 3.09 | 3.00 |
| 8* | — | 0.53 | 1.47 | 2.75 | 2.75 |
| 9 | — | — | 0.43 | 2.44 | 2.85 |
| 10 | — | — | 2.99 | 3.15 | 2.73 |
| 11 | — | 0.10 | 2.42 | 2.45 | 1.93 |
| 12 | — | — | — | 1.13 | 1.95 |
| 13 | — | — | — | — | 1.89 |
| 14 | — | — | — | — | — |
| 15 | — | — | — | — | — |
| 16 | — | — | — | — | — |
| 17 | — | 2.93 | 3.62 | 3.72 | 3.44 |
| 18 | — | — | 1.18 | 2.28 | 2.62 |
| 19 | — | — | 0.43 | 0.43 | 0.81 |
| 20 | — | 1.65 | 3.20 | 2.97 | 2.88 |

*The values were not corrected because no preimmune serum was available
"—" means optical density ($OD_{490}$) < 0.1

TABLE 2

Neutralization by sera from rabbits treated with BOTOX ® (week 11 after the first immunization) in the mouse hemidiaphragm assay (detection limit: 0.35 mU/ml antibodies)

| Rabbits | Neutralization mU/ml |
|---|---|
| 1 | 2.0 |
| 2 | n.d. |
| 3 | n.d. |
| 4 | >10 |
| 5 | >100 |
| 6 | n.d. |
| 7 | >10 |
| 8 | >10 |
| 9 | n.d. |
| 10 | n.d. |
| 11 | n.d. |
| 12 | >10 |
| 13 | n.d. |
| 14 | n.d. |
| 15 | <0.35 |
| 16 | 0.4 |
| 17 | >10 |
| 18 | >10 |
| 19 | 2.0 |
| 20 | >10 | n.d. = not determined

EXAMPLE 5

Antigenicity Assay with Market Product and Pure Neurotoxin

After it had been shown that the complex of neurotoxin and hemagglutinins and the nontoxic, non-hemagglutinating protein induces the formation of neutralizing antibodies, the immunogenic effect of the pure neurotoxin (type A) was tested. For this purpose, 8 rabbits were treated with the toxin complex and 12 rabbits were treated with the pure toxin. 25 U of the respective product were administered intracutaneously by the method described above (see Example 1). The amount of neurotoxin, measured by weight, was the same in both products (200 pg/dose), as was demonstrated in an ELISA. BOTOX® additionally contained complex proteins (about 800 pg/dose).

Four of the eight animals treated with BOTOX® showed an antibody titer in the ELISA, whereas no antibodies against the pure neurotoxin were detectable in the 12 animals treated with pure neurotoxin. The result was confirmed in the biological activity assay. All four rabbit sera contained neutralizing antibody titers preventing an effect of the toxin (Table 3).

TABLE 3

Neutralization by sera (diluted 1:3) from rabbits treated with BOTOX ® (week 11 after the first immunization) in the mouse hemidiaphragm assay (detection limit: 1 mU/ml antibodies)

| Rabbits | Neutralization mU/ml |
|---|---|
| 1 | 12 mU |
| 2 | >30 mU |
| 3 | 4.5 mU |
| 8 | >30 mU |

EXAMPLE 6

Comparative Example

This experiment compared the antibody formation due to BOTOX® with that due to DYSPORT®. For this purpose, groups of ten rabbits were treated either with BOTOX® (group 1), with DYSPORT® (group 2) or with the pure neurotoxin (group 3) in accordance with the scheme described.

Whereas more than 50% of the animals formed a neutralizing antibody titer in group 1 and 2, the sera from the animals in group 3 were free of antibodies.

EXAMPLE 7

Clinical Test

A patient (45 years of age) who had been treated for a period of 5 years with BOTOX® for spasmodic torticollis had developed an antibody titer of 3 mU/ml of serum. Neither BOTOX® nor DYSPORT® was therapeutically effective for this patient. An attempt at therapy with the pure botulinum neurotoxin in a dose of 145 U, which was equivalent to the last BOTOX dose injected, resulted within 72 hours in loosening of the muscle, normalization of the posture of the head and disappearance of the muscle pain. No adverse effects occurred.

EXAMPLE 8

Clinical Test

A patient (52 years of age) had been treated with BOTOX® for 3 years for cerebral palsy. He had developed an antibody titer of 1 mU/ml of serum and it was thus necessary to discontinue the therapy. Injection of 200 U of pure neurotoxin made successful therapy possible.

REFERENCES

DasGupta, B. R. & Sathyamoorthy, V. (1984), Purification and Amino Acid Composition of Type A Botulinum Neurotoxin; *Toxicon* 22(3), p. 415-424

De Jongh, K. S., Schwartzkoff, C. L. & Howden, M. E. H. (1989), *Clostridium botulinum* Type D Neurotoxin Purification and Detection; *Toxicon* 27(2), p. 221-228

Schmidt, J. J. & Siegel, L. S. (1986), Purification of Type E Botulinum Neurotoxin by High-Performance Ion Exchange Chromatography; *Analyt. Biochemistry* 156, p. 213-219

Nukina, M., Mochida, Y., Sakaguchi, S. & Sakaguchi, G. (1988), Purification of *Clostridium botulinum* Type G Progenitor Toxin; *Zbl. Bakt. Hyg. A* 268, p. 220-227

Terajima, J., Syuto, B., Ochandra, J. O. & Kubo, S. (1985), Purification and Characterization of Neurotoxin Produced by *Clostridium botulinum* Type C 6813; *Infection and Immunity* 48(2), p. 312-317

Wadsworth, J. D. F., Desai, M., Tranter, H. S. et al. (1990), Botulinum type F neurotoxin: Large-scale Purification and Characterization of its Binding to Rat Cerebrocortical Synaptosomes; *Biochem. J.* 268, p. 123-128

The invention claimed is:

1. A method of treating a human or animal with a cosmetic condition treatable with a botulinum neurotoxin, comprising administration, to the human or animal, a treatment effective amount of a botulinum neurotoxin from *Clostridium botulinum* of type A, B, C, D, E, F or G or a mixture of two or more botulinum neurotoxins, wherein the neurotoxin or mixture of neurotoxins is free of the complexing proteins which naturally form complexes with botulinum neurotoxins, and wherein the human or animal already exhibits neutralizing antibodies against botulinum neurotoxin complexes.

2. The method of claim 1 wherein the subject exhibits neutralizing antibodies against a complex of *Clostridium botulinum* type A or B or a complex of *Clostridium botulinum* type A and type B.

3. The method of claim 1 wherein the cosmetic treatment is for hyperhidrosis.

4. The method of claim 1 wherein the cosmetic treatment is for wrinkling.

5. The method of claim 4 wherein the cosmetic treatment is for facial wrinkling.

6. A method of treating a human or animal with dystonia or a nervous system disorder treatable with a botulinum neurotoxin, comprising administration, to the human or animal, a treatment effective amount of a botulinum neurotoxin from *Clostridium botulinum* of type A, B, C, D, E, F or G or a mixture of two or more botulinum neurotoxins, wherein the neurotoxin or mixture of neurotoxins is free of the complexing proteins which naturally form complexes with botulinum neurotoxins, and wherein the human or animal already exhibits neutralizing antibodies against botulinum neurotoxin complexes and is a secondary non-responder.

7. The method of claim 6 wherein the subject exhibits neutralizing antibodies against a complex of *Clostridium botulinum* type A or B or a complex of *Clostridium botulinum* type A and type B.

8. The method of claim 6 wherein the dystonia or disorder of the nervous system is selected from spasmodic torticollis, blepharospasm, spasticities such as footdrop, hemifacial spasms, migraine, low back pain, cervical spine disorders and hypersalivation.

* * * * *